United States Patent [19]

Meyers et al.

[11] Patent Number: 5,882,665
[45] Date of Patent: Mar. 16, 1999

[54] PHYTOSPHINGOSINE SALICYLATES IN COSMETIC COMPOSITIONS

[75] Inventors: Alan Joel Meyers, Trumbull; Joseph Michael Corey, Waterbury; Anthony Vargas, Monroe, all of Conn.

[73] Assignee: Elizabeth Arden Co., Division of Conopco, Inc., New York, N.Y.

[21] Appl. No.: 971,794

[22] Filed: Nov. 18, 1997

[51] Int. Cl.$^6$ ........................................ A61K 7/00
[52] U.S. Cl. .................... 424/401; 514/859; 514/887; 514/547
[58] Field of Search ............................. 424/401; 514/547, 514/887, 859

[56] References Cited

U.S. PATENT DOCUMENTS 5,326,565  7/1994  Critchley et al. ........................ 424/401
5,578,641  11/1996  Jackson .................................... 514/547

*Primary Examiner*—Thurman K. Page
*Assistant Examiner*—D. Faulkner
*Attorney, Agent, or Firm*—Milton L. Honig

[57] ABSTRACT

A novel series of phytosphingosines are disclosed which are phytosphingosine salicylates having use in cosmetic compositions. They have potential as anti-acne, anti-blemish, anti-bacterial and anti-wrinkle agents, as well as being active in skin lightening.

2 Claims, No Drawings

PHYTOSPHINGOSINE SALICYLATES IN COSMETIC COMPOSITIONS

BACKGROUND OF THE INVENTION

1. Field of the Invention

The invention concerns new phytosphingosine derivatives and their use in cosmetic compositions.

2. The Related Art

Ceramides represent an important group of lipids, members of which are found in the epidermis of mammals. Skin ceramides are believed to play an important role in water permeability properties, providing an epidermal water-barrier functioning to give increased strength to skin structure and to decrease water loss. Ceramides are N-acylated sphingosine bases. Sphingosine bases are of variable chain length and have the general formula:

where A is $-CH=CH-$ (sphingosine), $-CH_2-CHOH-$ (phytosphingosine) or $-CH_2CH_2-$ (dihydrosphingosine), and where x is generally in the broad range 7 to 27, more typically in the range 10 to 16. Seven distinguishable groups of ceramides have been identified in pig and human epidermis. Each group consists of molecules of varying fatty acid chain length.

Besides naturally occurring ceramides there are substances closely related to them which have been disclosed as components of skin care compositions. For instance, U.S. Pat. No. 5,326,565 (Critchley et al.) reports on a series of novel pseudoceramides which can be prepared at lower cost while still retaining properties necessary to improve water barrier function of the stratum corneum.

Beyond the control of water permeability properties, modified phytosphingosines may have other useful cosmetic properties. Such properties include anti-acne, anti-blemish, anti-bacterial and anti-wrinkle effectiveness.

Accordingly, it is an object of the present invention to provide new types of phytosphingosine derivatives which may be cosmetically useful.

Another object of the present invention is to provide methods for treating acne, blemishes, age spots, fine lines and wrinkles, bacterial growth, oily secretion from pores and the general signs of aging and for lightening (whitening) skin.

These and other objects of the present invention will become more readily apparent from consideration of the following summary and detailed description.

SUMMARY OF THE INVENTION

Novel phytosphingosine compounds are provided having the structure (I):

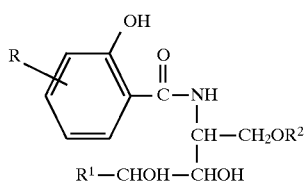

wherein:

R represents a linear or branched, saturated or unsaturated, hydroxylated or non-hydroxylated aliphatic hydrocarbon group having from 1 to 49 carbon atoms or a subgroup (II):

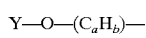

a is an integer of from 7 to 50;
b is an integer of from 10 to 100;
m is 0 or 1;
Y represents H or a $C_{14}$–$C_{22}$ fatty acid having general structure (III):

wherein:
z is —OH or an epoxy oxygen;
x is an integer of from 12 to 20;
y is an integer of from 20 to 40; and
z is 0 or an integer of from 1 to 4;
$R^1$ represents a linear or branched, saturated or unsaturated, hydroxylated or non-hydroxylated aliphatic hydrocarbon group having from 8 to 28 carbon atoms; and
$R^2$ represents H, a phosphate, a sulfate or a sugar.

DETAILED DESCRIPTION OF THE INVENTION

Now it has been discovered that salicylates of phytosphingosine can have activity against acne, blemishes, bacterial growth, fine lines and wrinkles and the general signs of aging. They also may be useful to lighten or whiten skin as well as control sebum generation, more specifically control of oil generated from skin pores.

The phytosphingosine derivatives of the present invention have the general structure (I):

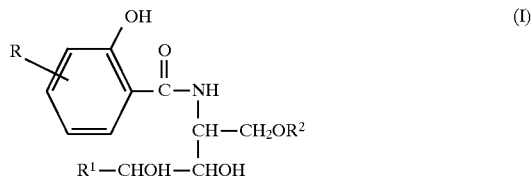

wherein:

R represents a linear or branched, saturated or unsaturated, hydroxylated or non-hydroxylated aliphatic hydrocarbon group having from 1 to 49 carbon atoms or a subgroup (II):

a is an integer of from 7 to 50;
b is an integer of from 10 to 100;
m is 0 or 1;
Y represents H or a $C_{14}$–$C_{22}$ fatty acid having general structure (III):

wherein:
z is —OH or an epoxy oxygen;
x is an integer of from 12 to 20;
y is an integer of from 20 to 40; and
z is 0 or an integer of from 1 to 4;
$R^1$ represents a linear or branched, saturated or unsaturated, hydroxylated or non-hydroxylated aliphatic hydrocarbon group having from 8 to 28 carbon atoms; and
$R^2$ represents H, a phosphate, a sulfate or a sugar.

Specific examples of phytosphingosine salicylates are those having the structures (IV) to (XVI):

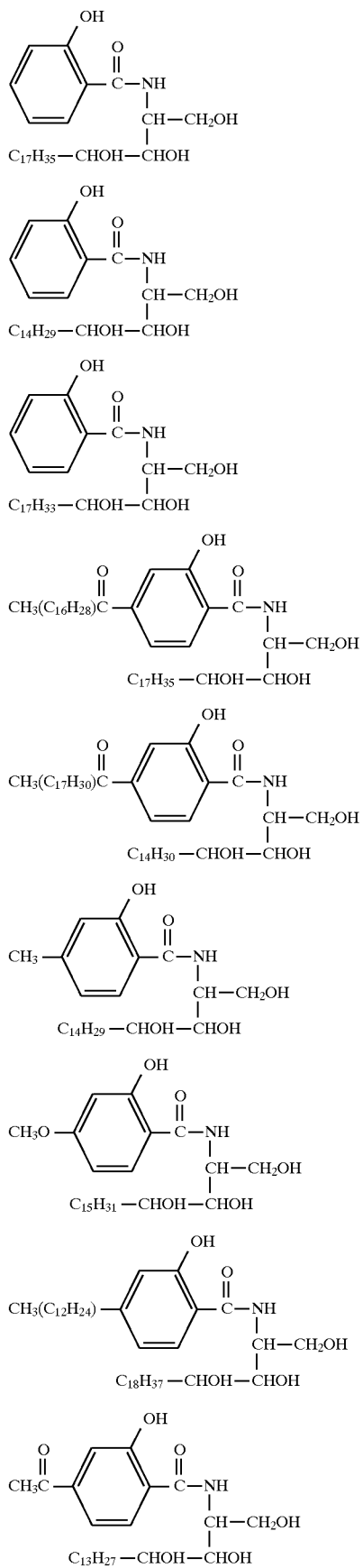

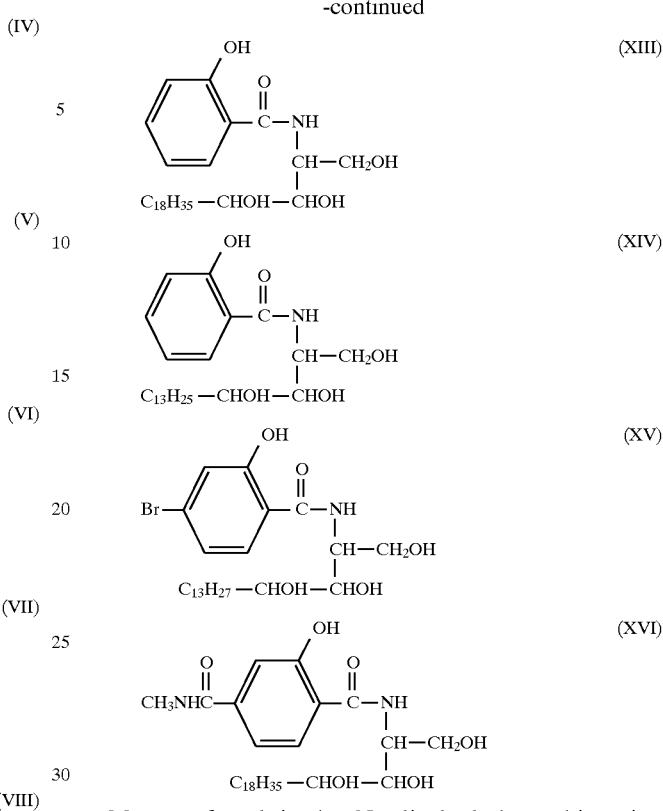

Most preferred is the N-salicyloyl-phytosphingosine known as N-[(1S,2S,3R)-2,3-dihydroxy-(1-hydroxymethyl)-heptadecyl)-salicylamide represented above by the structure V.

The amount of phytosphingosine derivative present in cosmetic compositions may range anywhere from 0.00001 to 3%, preferably from 0.0001 to 0.5%, more preferably from 0.001 to 0.1%, optimally from 0.01 to 0.05% by weight.

Cosmetic compositions incorporating the phytosphingosine derivatives of this invention may be anhydrous or hydrous. When containing water they may be fully aqueous or mixtures of an aqueous and oily phase forming emulsions. Water constituting the aqueous phase may be present in amounts from 1 to 90%.

Emollient oils can form the oily phase of emulsions. These emollient oils may be in the form of hydrocarbons, silicones, synthetic or natural esters and combinations thereof. Amounts of the emollient oil will range from about 0.1 to about 30%, preferably from about 0.5 to about 10%, optimally from about 0.5 to about 3% by weight.

Hydrocarbons may be present in the form of mineral oil, terpenes (such as squalene), isoparaffins and petroleum jelly.

Silicone oils may be divided into the volatile and nonvolatile variety. The term "volatile" as used herein refers to those materials which have a measurable vapor pressure at ambient temperature. Volatile silicone oils are preferably chosen from cyclic or linear polydimethylsiloxanes containing from about 3 to about 9, preferably from about 4 to about 5, silicon atoms. Linear volatile silicone materials generally have viscosities less than about 5 centistokes at 25° C. while cyclic materials typically have viscosities of less than about 10 centistokes. Examples of commercially available volatile silicone oils are Dow Corning® 344 and Dow Corning® 345.

Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 10 to about 400 centistokes at 25° C.

Silicone copolyols are particularly useful as emollient and emulsifying materials within the context of the present invention. Particularly preferred is Dow Corning® 3225C fluid, a mixture of cyclomethicone and dimethicone copolyol having viscosity at 25° C. of 600–2000 cps and a specific gravity of about 0.963.

Among the ester emollients are:

(1) Alkenyl or alkyl esters of fatty acids having 10 to 45 carbon atoms. Examples thereof include isoarachidyl neopentanoate, isononyl isononanoate, oleyl myristate, oleyl stearate, octyl stearate, oleyl oleate, isononyl octanoate, octyl isononanoate and arachidyl erucate.

(2) Ether-esters such as fatty acid esters of ethoxylated fatty alcohols.

(3) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(4) Wax esters such as beeswax, spearmaceti, myristyl myristate, stearyl stearate.

(5) Mono-, Di- and Triglyceride esters such as PEG-8 caprylic/capric triglyceride.

(6) Sterols esters, of which cholesterol fatty acid esters are examples thereof.

Sunscreen agents may also be included in the cosmetic compositions. These agents may either be organic or inorganic materials. Illustrative inorganic actives are such materials as microfine titanium dioxide, zinc oxide, polyethylene, nylon, polymethacrylate and various other polymers all of whom when incorporated into a cosmetic composition will protect against ultraviolet light in the range from 290 to 400 nm. The organic sunscreen agents will have at least one chromophoric group absorbing within the ultraviolet range so as also to prevent 290 to 400 nm radiation penetrating to the skin. Typical sunscreen agents include octyl methoxycinnamate (Parsol MCX®), octocrylene (Uvinul N-539®), butyl methoxy dibenzoyl methane (Parsol 1789®) and oxybenzone. These may be present in amounts from 0.1 to 30% by weight.

Optionally there may be present in the cosmetic compositions of the present invention a variety of other materials. Examples include fatty acids, humectants, thickeners/viscosifiers, surfactants, preservatives, biologically active materials and minor adjunct ingredients. These are described more fully below.

Fatty acids having from 8 to 30 carbon atoms may be included in the compositions of this invention. Illustrative of this category are pelargonic, lauric, myristic, palmitic, stearic, isostearic, hydroxystearic, oleic, linoleic, ricinoleic, arachide, behenic and erucic acids. Amounts may range from 0.1 to 30% by weight.

Humectants of the polyhydric alcohol-type may be included in the compositions of this invention. The humectant aids in increasing the effectiveness of the emollient, reduces scaling, stimulates removal of built-up scale and improves skin feel. Typical polyhydric alcohols include glycerol (known also as glycerin), polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol. The amount of humectant may range anywhere from 0.5 to 30%, preferably between 1 and 15% by weight of the composition.

Surfactants may be included in the compositions of this invention. total concentration of the surfactant will range from about 0.1 to about 40%, preferably from about 1 to about 20%, optimally from about 1 to about 5% by weight of the total composition. The surfactant may be selected from the group consisting of anionic, nonionic, cationic and amphoteric actives. Particularly preferred nonionic surfactants are those with a $C_{10}$–$C_{20}$ fatty alcohol or acid hydrophobe condensed with from about 2 to about 100 moles of ethylene oxide or propylene oxide per mole of hydrophobe; the $C_2$–$C_{10}$ alkyl phenols condensed with from 2 to 20 moles of alkylene oxide; mono- and di-fatty acid esters of ethylene glycol; fatty acid monoglyceride; sorbitan, mono- and di-$C_8$–$C_{20}$ fatty acids; and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_8$–$C_{20}$ acyl isethionates and combinations thereof.

Compositions of the present invention may also contain $C_1$–$C_{20}$ α-hydroxycarboxylic acids and salts thereof. The salts are preferably alkalimetal, ammonium and $C_1$–$C_{12}$ alkanolammonium salts. Illustrative acids are glycolic acid, lactic acid and 2-hydroxycaprylic acid. Most preferred is a combination of lactic and 2-hydroxycaprylic acids and their ammonium salts. Levels of these materials may range from about 0.01 to about 15%, preferably from about 0.1 to about 9%, optimally between about 0.5 and about 7% by weight of the cosmetic composition.

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are disodium EDTA, phenoxyethanol, methyl paraben, propyl paraben, imidazolidinyl urea (commercially available as Germall 115®), sodium dehydroacetate and benzyl alcohol.

The preservatives should be selected having regard for the use of the composition and possible incompatibilities between the preservatives and other ingredients in the emulsion. Preservatives are preferably employed in amounts ranging from about 0.01% to about 2% by weight of the composition.

Minor adjunct ingredients may also be present in the cosmetic compositions These ingredients include vitamins (such as Vitamin $B_6$, Vitamin C, ascorbyl palmitate, Vitamin A palmitate, Vitamin E acetate, biotin, niacin and DL-panthenol), amino acids (such as glycine and serine), ceramides (such as Ceramide I, III and VI), biohyaluronic acid with oligosaccharides (available as Actiglide J® Special from Active Organics US) and sodium PCA.

Natural vegetable materials from renewable resources are often desirable in cosmetic compositions. For instance, cosmetic compositions of the present invention may include ß2-glucan derived from oats, commercially available under the trademark Microat CP from Nurture Inc., Missoula, Mont. Another natural material is plant pseudocollagen commercially available from Brooks, Inc., South Plainfield, N.J. Amounts of each of the foregoing materials may range from about 0.001 to about 10%, preferably from about 0.05 to about 1%, optimally between about 0.1 and 0.5% b weight.

Colorants, fragrances, opacifiers and abrasives may also be included in compositions of the present invention. Each of these substances may range from about 0.005 to about 5%, preferably between 0.1 and 3% by weight.

The following Examples will more fully illustrate the embodiments of this invention. All parts, percentages and proportions referred to herein and in the appended claims are by weight unless otherwise indicated.

EXAMPLE 1

Synthesis of N-salicyloyl-phytosphingosine

In a 100 ml three-necked flask equipped with dropping funnel, reflux condenser and nitrogen inlet tube, is placed 27 ml (0.45 mol) of monoethanolamine. While stirring and heating the mixture at 80° C. under a nitrogen atmosphere, a solution of 10 g (0.037 mol) of 1,2-epoxyoctadecane is added dropwise over 15 minutes. After the addition is complete, heating and stirring are continued for an additional two hours under the same conditions. The reaction mixture is cooled to 50° C., hexane (50 ml) is added and the resulting solution is extracted at 60° C. with two portions 40 ml each of hot water. The hexane layer is separated; on cooling a white solid is precipitated which can be collected and recrystallized from first hexane and then methanol. This material is identified as N-(2-hydroxyethyl)-2-hydroxyoctadecylamine), hereinafter referred to as phytosphingosine.

In a 50 ml two necked flask equipped with a vacuum inlet tube is placed 0.03 g of potassium hydroxide and 2.0 g (0.006 mol) of phytosphingosine. While stirring and heating the resultant mixture at 85° C., 20 Torr, 1.75 g of methyl salicylate is added proportion wise over 15 minutes. After the addition is complete, the mixture is stirred for a further 3 hours under the same conditions. The product is purified by two recrystallizations from hexane to give N-(2-hydroxyoctadecyl)-N-(2-hydroxyethyl)-2-salicylamide.

EXAMPLE 2

A typical cosmetic composition for delivering phytosphingosine derivatives has the following formula.

TABLE I

| COMPONENT | WEIGHT % |
| --- | --- |
| Butylene Glycol | 3.00 |
| Stearic Acid | 3.00 |
| Finsolv TN7 | 2.50 |

TABLE I-continued

| COMPONENT | WEIGHT % |
| --- | --- |
| Ceraphyl 2307 | 2.50 |
| Ammonia (Aqueous 26BE) | 2.20 |
| Glycerin | 2.00 |
| Myrj 597 | 2.00 |
| Polyethylene Imine | 2.00 |
| Stearyl Alcohol | 1.50 |
| Glycerol Monostearate | 1.50 |
| Triethanolamine (99%) | 1.20 |
| Magnesium Aluminum Silicate | 1.00 |
| SE 700 | 1.00 |
| Silicone Fluid 10 | 1.00 |
| Arlacel 607 | 1.00 |
| Dow Corning 14017 | 0.80 |
| Jaguar HP-1207 | 0.50 |
| Disodium EDTA | 0.50 |
| Sodium Stearoyl Lactylate | 0.50 |
| Cholesterol | 0.30 |
| Fragrance | 0.30 |
| Tween 807 | 0.30 |
| Methylparaben | 0.15 |
| Antifoam Emulsion | 0.10 |
| Vitamin E Acetate | 0.10 |
| Propylparaben | 0.10 |
| Hydroxycaprylic Acid | 0.10 |
| Vitamin A Palmitate | 0.10 |
| Bisabolol | 0.10 |
| Phytosphingosine Salicylate | 0.10 |
| Water | qs |

EXAMPLE 3

Another cosmetic composition including phytosphingosine derivatives according to the present invention has the formula as listed below.

TABLE II

| COMPONENT | WEIGHT % |
| --- | --- |
| Propylene Glycol Isoceteth-3 Acetate | 14.00 |
| Octyl Dodecyl neopentanoate | 14.00 |
| Potassium L-Lactate | 13.00 |
| Parsol MCX7 | 5.00 |
| Parsol 17897 | 4.00 |
| Lanolin Extract ($C_{14}$–$C_{22}$ AHA Fraction) | 4.00 |
| Zinc Oxide | 3.00 |
| Dimethicone Copolyol Phosphate | 3.00 |
| PEG-20 Sorbitan Isostearate | 2.00 |
| Isostearic Acid | 1.75 |
| Polyoxyethylene (21) Stearyl Ether | 1.50 |
| Magnesium Aluminum Silicate | 0.70 |
| Propylene Glycol | 0.50 |
| Glycerin | 0.50 |
| Triethanolamine | 0.35 |
| Xanthan Gum | 0.20 |
| Polyoxyethylene (2) Stearyl Ether | 0.20 |
| Glydant Plus ® | 0.20 |
| Fragrance | 0.20 |
| Botanical Blend | 0.10 |
| Vitamin E Linoleate | 0.10 |
| Aloe Vera Gel | 0.01 |
| Phytosphingosine Salicylate | 0.01 |
| Water | qs |

EXAMPLE 4

A still further cosmetic composition illustrating use of phytosphingosine derivatives according to the present invention is provided in the following formulation.

TABLE III

| COMPONENT | WEIGHT % |
| --- | --- |
| L-Lactic Acid | 7.00 |
| Triethanolamine | 3.00 |
| Alkyl Polyglycoside | 3.00 |
| Cetyl Alcohol | 2.50 |
| Glycerol Monostearate | 2.00 |
| Octyl Palmitate | 2.00 |
| Silicone Fluid | 1.50 |
| Petroleum Jelly | 1.00 |
| Methyl Paraben | 0.15 |
| Propyl Paraben | 0.10 |
| Fragrance | 0.10 |
| Phytosphingosine Salicylate | 0.01 |
| Water | qs |

EXAMPLE 5

Still another cosmetic composition with phytosphingosine derivatives of the present invention is that provided in the formula below.

TABLE IV

| COMPONENT | WEIGHT % |
| --- | --- |
| Isopropyl Myristate | 3.00 |
| Stearic Acid | 3.00 |
| Propylene Glycol | 3.00 |
| Cyclomethicone | 3.00 |
| L-Lactic Acid | 2.00 |
| Panthenol | 1.00 |
| Ammonia (Aqueous 26 BE) | 1.00 |
| Disodium EDTA | 0.10 |
| Fragrance | 0.10 |
| Sodium Sorbate | 0.10 |
| Phytosphingosine Salicylate | 0.10 |
| Water | qs |

EXAMPLE 6

Yet another cosmetic composition illustrative of phytosphingosine salicylate formulations has the formula provided below.

TABLE V

| COMPONENT | WEIGHT % |
| --- | --- |
| Cyclomethicone | 48.10 |
| Ethyl Alcohol | 24.70 |
| Isopropyl PPG-2 Isodeceth-7-carboxylate | 10.00 |
| Ammonium Glycolate | 7.00 |
| Potassium Alpha-hydroxyhexadecanoate | 5.50 |
| Propylene Glycol Dicaprylate/Dicaprate | 4.00 |
| Hydroxycaprylic Acid | 0.50 |
| Phytosphingosine Salicylate | 0.20 |

The foregoing description and examples illustrate selected embodiments of the present invention. In light thereof variations and modifications will be suggested to one skilled in the art, all of which are within the spirit and purview of this invention.

What is claimed is:

1. A compound with the structure:

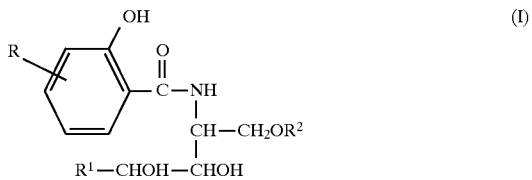

wherein:

R represents a linear or branched, saturated or unsaturated, hydroxylated or non-hydroxylated aliphatic hydrocarbon group having from 1 to 49 carbon atoms or a subgroup (II):

a is an integer of from 7 to 50;
b is an integer of from 10 to 100;
m is 0 or 1;

Y represents H or a $C_{14}-C_{22}$ fatty acid having general structure (III):

wherein:
z is —OH or an epoxy oxygen;
x is an integer of from 12 to 20;
y is an integer of from 20 to 40; and
z is 0 or an integer of from 1 to 4;

$R^1$ represents a linear or branched, saturated or unsaturated, hydroxylated or non-hydroxylated aliphatic hydrocarbon group having from 8 to 28 carbon atoms; and $R^2$ represents H, a phosphate, a sulfate or a sugar.

2. The compound according to claim 1 which is N-(2-hydroxyoctadecyl)-N-(2-hydroxyethyl)-2-salicylamide.

* * * * *